(12) United States Patent
Giarratana et al.

(10) Patent No.: US 8,206,979 B2
(45) Date of Patent: Jun. 26, 2012

(54) METHOD FOR PRODUCING RED BLOOD CELLS

(75) Inventors: Marie-Catherine Giarratana, Saint-Ouen (FR); Luc Douay, Paris (FR)

(73) Assignee: Universite Pierre et Marie Curie — Paris VI, Paris (FR)

( * ) Notice: Subject to any disclaimer, the term of this patent is extended or adjusted under 35 U.S.C. 154(b) by 170 days.

(21) Appl. No.: 11/597,509

(22) PCT Filed: Mar. 11, 2005

(86) PCT No.: PCT/IB2005/000626
§ 371 (c)(1),
(2), (4) Date: Jan. 29, 2007

(87) PCT Pub. No.: WO2005/118780
PCT Pub. Date: Dec. 15, 2005

(65) Prior Publication Data
US 2007/0218552 A1 Sep. 20, 2007

Related U.S. Application Data

(60) Provisional application No. 60/576,936, filed on Jun. 4, 2004.

(51) Int. Cl.
*C12N 5/00* (2006.01)
*C12N 5/10* (2006.01)
(52) U.S. Cl. .......................... 435/373; 435/372; 435/325
(58) Field of Classification Search .................. 435/373, 435/372, 324, 2
See application file for complete search history.

(56) References Cited

U.S. PATENT DOCUMENTS

| | | | |
|---|---|---|---|
| 5,599,705 A | | 2/1997 | Cameron |
| 5,670,351 A | * | 9/1997 | Emerson et al. ............... 435/440 |
| 6,548,299 B1 | * | 4/2003 | Pykett et al. ................... 435/377 |
| 2003/0022825 A1 | * | 1/2003 | Nishikawa et al. ............. 514/12 |

FOREIGN PATENT DOCUMENTS
WO 99/64566 12/1999

OTHER PUBLICATIONS

Kobari et al Exp Hematol. Dec. 2000;28(12):1470-80.*
Sato et al J Clin Invest, 2000.106(2): 263-70.*
Yanai et al Leukemia. Apr. 1997;11 Suppl 3:484-5.*
Lane et al Blood, 1995, 275-282.*
"Impact of the Microenvironment on the Ex Vivo Capacity of Cord Blood or Bone Marrow Erythroid Precursors to Differentiate Into Enucleated Red Blood Cells," M.C. Giarratana et al., Abstracts/Experimental Hematology, vol. 31, No. 7, Jul. 2003, p. 138, XP-002334364.
"Human Erythroid Cells Produced Ex Vivo at Large Scale Differentiate Into Red Blood Cells in Vivo," Neildez-Nguyen et al., Research Article, vol. 20, May 2002, Nature Biotechnology, XP-002334360.
"An in Vitro Model of Human Red Blood Cell Production From Hematopoietic Progenitor Cells," Punam Malik et al., Rapid Communication, vol. 91, No. 8, Apr. 15, 1998, pp. 2664-2671, XP-002127093.
"Erythropoietin-independent Erythrocyte Production: Signals through gp130 and c-kit Dramatically Promote Erythropoiesis from Human CD34 Cells," Xingwei Sui et al., Journal of Experimental Medicine, vol. 183, No. 3, 1996, pp. 837-845, XP-002334361.
"Characterization of Murine Hemopoietic-Supportive (MS-1 and MS-5) and Non-Supportive (MS-K) Cell Lines," Jun Suzuki et al., Leukemia (Basingstoke), vol. 6, No. 5, 1992, pp. 452-458, XP-009050220.

* cited by examiner

*Primary Examiner* — Anoop Singh
(74) *Attorney, Agent, or Firm* — Young & Thompson

(57) ABSTRACT

The invention relates to a method for the expansion and differentiation of haematopoietic stem cells into enucleated erythrocytes, in two steps: a first step in a culture medium, where cell proliferation and erythmid differentiation are induced in the presence of growth factors, and a second step modeling a reconstitution of the microenvironment, substantially without erythropoietin (EPO). Optionally, the method of culture may comprise an intermediate step, with haematopoietic growth factors.

11 Claims, 9 Drawing Sheets

US 8,206,979 B2

METHOD FOR PRODUCING RED BLOOD CELLS

This application is s a National Stage Application of PCT/IB2005/000626, filed Mar. 11, 2005, which claims priority to U.S. Provisional Application 60/576,936, filed Jun. 4, 2004.

FIELD OF INVENTION

The present invention relates to the production of red blood cells, and more particularly to an in vitro method for massive and selective production of enucleated erythrocytes.

BACKGROUND OF INVENTION

One of the major characteristics of the human Red Blood Cell (RBC) is to be the only cell to have a prolonged life span (120 days) despite the absence of a nucleus. The mechanisms of enucleation are suspected (Bessis, 1958; Lichtman, 1981; Qiu et al., 1995), but have not been formally established due to a lack of experimental conditions permitting the massive ex vivo generation of RBCs.

In adult humans, in vivo hematopoiesis results from a dynamic production process situated in the bone marrow, which starts from a minor population of haematopoietic stem cells (HSCs) according to a pyramidal cellular hierarchy (Stem Cell (SC), progenitor and maturation compartments) (Ogawa, 1993) and operates in close contact with the microenvironment (Lemischka, 1997; Friedenstein, 1977; Verfaillie, 1993). In vitro erythropoietic microenvironments were developed in vitro, showing the importance of contact between the hematopoietic and adherent cells (Ohneda et al., 1997; Yanai et al., 1997; Hanspal et al., 1994; Hanspal et al., 1998)). Furthermore erythropoiesis is known to be positively regulated by stem cell factor (SCF), interleukin (IL3), and erythropoietin (EPO) (Zermati et al., 2000; Sato et al., 2000; Dolznig et al., 2002).

If it is apparently easy to obtain almost complete erythroid differentiation (Fibach et al., 1989; Wada et al., 1990; Panzenbock et al., 1998; Freyssinier et al., 1999), the literature data nevertheless show, on reaching the final stage of the different methods of culture proposed, either an important cell proliferation without terminal maturation (Sui et al., 1996; von Lindern et al., 1999), or enucleation in about half of the cells but with a reduced level of amplification (Malik et al., 1998). No set of ex vivo conditions has yet been reported which allows to obtain both a massive proliferation and total enucleation of the erythroblasts.

The expansion of HSCs derived from Cord Blood (CB) in a well-defined stroma-free medium, has been described based on the sequential addition of growth factors (Neildez-Nguyen et al., 2002). Starting from CD34+ cells, this protocol enabled the massive production of pure erythroid precursors that were yet incapable to reach maturation into enucleated cells.

The interest of producing erythrocyte precursors for infusion was reviewed in L. Douay, 2003.

SUMMARY OF THE INVENTION

The inventors have now designed a protocol for the expansion and differentiation of haematopoietic stem cells into enucleated erythrocytes, in two steps: a first step in a culture medium, where cell proliferation and erythroid differentiation are induced in the presence of growth factors, and a second step modeling a reconstitution of the microenvironment, preferably with no haematopoietic growth factors. Optionally, the method of culture may comprise an intermediate step, in the presence of both the microenvironment and haematopoietic growth factors.

The inventors have shown that this method of culture allows both for the massive expansion of CD34+ SCs/progenitors and their complete differentiation into perfectly functional mature RBCs, which survive in vivo in NOD/SCID mice as do RBCs from human peripheral blood.

The mature RBCs have all the characteristics of adult and functional native RBCs.

This method is hence particularly useful for massive production of mature red cells, for clinical transfusion.

DETAILED DESCRIPTION OF THE INVENTION

Figure 1A:
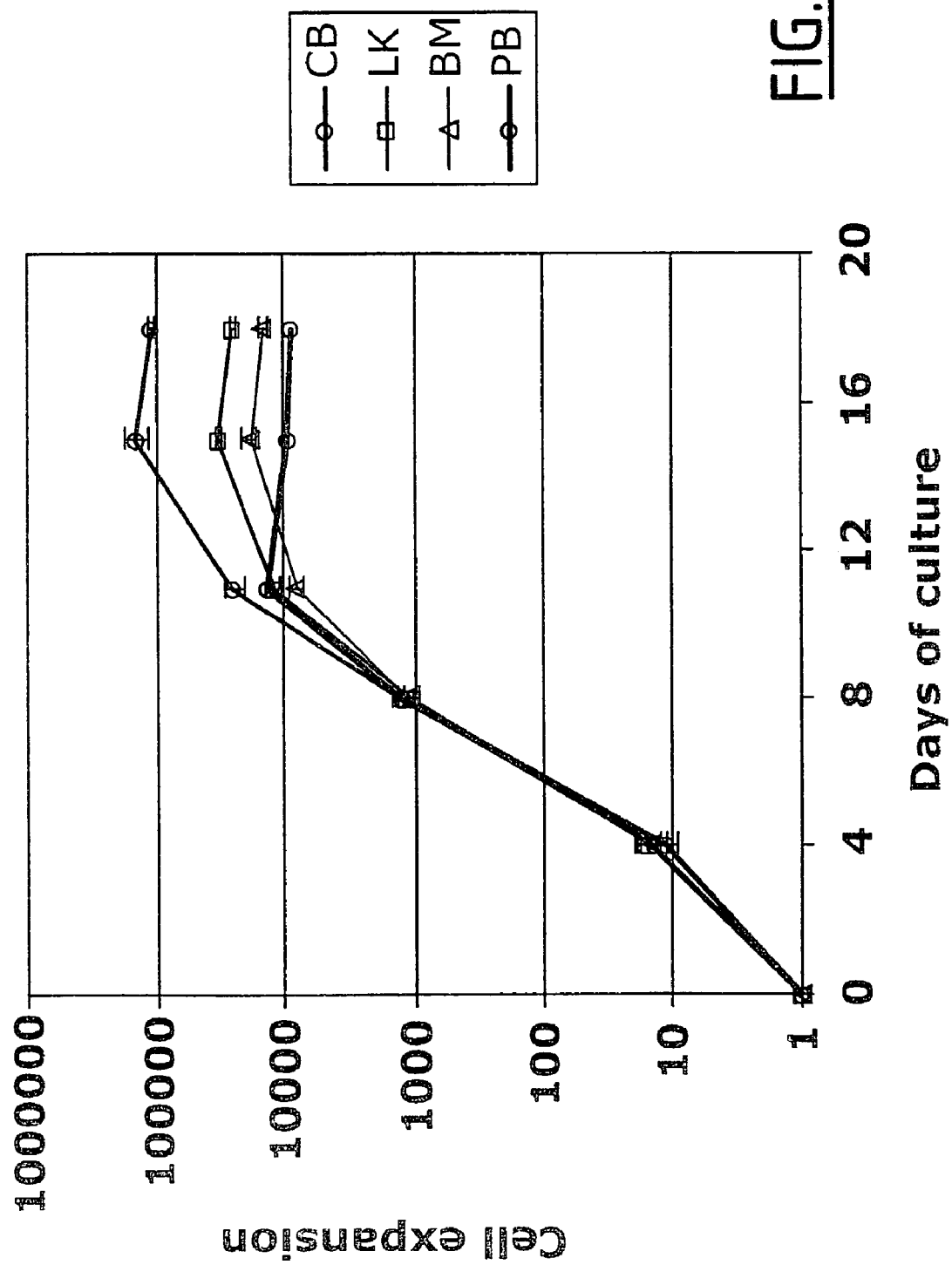
FIG. 1: Massive amplification of erythroid cells. (A) Human $CD34^+$ cells from cord blood (CB), bone marrow (BM), peripheral blood (PB) or leukapheresis (LK) were cultured in a liquid medium on a layer of stromal cells of murine origin (MS5) according to a three phase protocol (see Materials and Methods, example 1) and total numbers of viable, non adherent cells were determined at different times. Mean values for cultures from 7 CB, 5 BM, 1 PB and 3 G-CSF-mobilized leukapheresis units are shown. (B) Photographs of the cells on days 0, 8, 11, 15 and 18 of culture after May-Grunwald-Giemsa staining. (C) Progenitor cell counts in semisolid cultures. Results are mean values (per $10^4$ seeded cells) for erythroid (CFU-E, BFU-E) and granulo-macrophagic (CFU-GM) progenitors in 4 independent experiments using cells from CB cultures. At various time points, aliquots of non adherent cells were grown in methylcellulose in the presence of SCF, GM-CSF, G-CSF, IL3 and Epo for progenitor evaluation.

The present invention thus provides an in vitro method for producing enucleated erythrocytes (including reticulocytes and mature red blood cells), which method comprises the steps of:

a) culturing haematopoietic stem cells in a culture medium that comprises at least a haematopoietic growth factor;

c) culturing the cells so obtained, in contact with supporting cells, substantially in the absence of EPO.

Optionally, the method comprises an intermediate additional step between step a) and step c) of:

b) culturing the cells obtained in step a), in a culture medium that comprises at least a haematopoietic growth factor and in contact with supporting cells.

The Starting Cells

The starting cells are haematopoietic stem cells that can be of any source. They are preferably of human origin. The haematopoietic stem cells may be obtained from a patient. They may be prepared from any biological sample, such as blood, e.g. peripheral blood, bone marrow, cord blood or fetal liver. For instance blood samples may be normal Peripheral Blood mobilized with G-CSF [Leukapheresis (LK)] or not (PB). The haematopoietic stem cells can be isolated using commercially available antibodies that bind to haematopoietic stem cell surface antigens, e.g. CD34, using methods known to those of skill in the art. For example, the antibodies may be conjugated to magnetic beads and immunological procedures utilized to recover the desired cell type. Preferably the haematopoietic stem cells are in the form of CD34$^+$ cells. Indeed CD34 is a standard marker for hematopoietic stem cells, as described in Baum et al., (1992) and Morrison et al., (1995). Separation of CD34$^+$ cells can be achieved by a number of different methods. The most widely used is a positive immunological selection based on binding of these cells to anti-CD34-antibodies immobilized on a solid support (Cellpro, Baxter, Myltenyi). Other selection methods include negative selection where all cells not expressing CD34 are isolated away from the CD34$^+$ cells based on their expression of lineage specific cell surface antigens Alternatively the haematopoietic stem cells to be cultured in step a) may be produced ex vivo from embryonic stem cells (see e.g. WO 01/34776; U.S. Pat. No. 6,613,568).

The haematopoietic stem cells cultured in step a) and the cells resulting from step a) can also be genetically modified cells. They can have been subjected to gene silencing, e.g. by homologous recombination, which means that they are no longer capable of expressing an endogenous gene, or the gene or a fragment thereof, has been deleted or "knocked-out". This is particularly useful to study the function of the silenced gene. The haematopoietic cells may also be genetically modified so that the erythrocytes produced therefrom would not express antigen of blood group. Alternatively the haematopoietic cells may be genetically modified by incorporation of genetic material into the cells, for example using recombinant expression vectors. The haematopoietic cells can then be capable of expressing an exogenous nucleotide sequence of interest. As an example, the sequence of interest may encode a haemoglobin antigen. Other examples of genetic material for introduction into haematopoietic cells include those which express gene products which have a role in haematopoietic stem cell maintenance, tissue development, remodelling, repair or in vivo production of extracellular gene products. Using genetically modified haematopoietic cells allows for the production of enucleated cells, which by definition can no longer divide and have been genetically modified to express certain surface proteins of therapeutic interest during a finite life span.

The Culture Media

The cells are cultured in culture media that preferably are in liquid form.

The culture media useful in the present invention may be any culture media known to the skilled person for culturing haematopoietic cells. For example, the culture medium may be RPMI, Iscove's MDM or DMEM, TC 199, X-VIVO-10, preferably with addition of human or fetal calf serum. Serum or plasma can be added at a concentration of 1 to 50%. However it is preferably a serum-free medium.

In a most preferred embodiment, the cells are cultured in a modified serum-free medium (Kobari et al. 2000; Giarratana et al. 2000) supplemented with 1% deionized Bovine Serum Albumin (BSA) or human serum albumin (HSA), 120 µg/ml iron-saturated human transferrin, 900 ng/ml ferrous sulfate, 90 ng/ml ferric nitrate and 10 µg/ml insulin.

The culture media of steps (c) and (b) comprise haematopoietic growth factors. Said growth factors include any or all Interleukins (IL-1 to IL-16), interferons (IFN-alpha, beta and gamma), erythropoietin (EPO), stem cell factor (SCF), insulin like growth factors, fibroblast growth factors, platelet-derived growth factor, tumor growth factor beta, tumor necrosis factor alpha, granulocyte colony stimulating factor (G-CSF), granulocyte-macrophage colony stimulating factor (GM-CSF), macrophage colony stimulating factor (M-CSF), fins-like tyrosine kinase-3 ligand (Flt3-ligand), as well as EGF (epidermal growth factor), VEGF (vascular endothelial growth factor), LIF (leukemia inhibiting factor). Thrombopoletin (TPO) or MGDF (mast growth derived factor) may also be used. Many of these growth factors are commercially available. Most commonly used mixture of growth factors includes G-CSF, GM-CSF, SCF, IL-1, IL-3 and IL-6. Most of the growth factors used are produced by recombinant DNA techniques are purified to various degrees. Some growth factors are purified from culture media of tumor cell lines by standard biochemical techniques. A widely used growth factor is PIXY 321 which is produced by recombinant technology and exhibits both, GM-CSF and IL-3 activity.

The culture medium of step a) preferably comprises SCF or a FLT-3 ligand. The growth factor used in step a) may also be selected from the group consisting of IL3, IL6, EPO and MGDF, or a mixture thereof. The combination of the growth factors may vary throughout step a). For instance, step a) may start with 8 days of SCF+EPO+IL3, and go on with 3 days of SCF+EPO. Advantageously a growth factor of step (a) is erythropoietin. In a preferred embodiment, the culture medium of step a) comprises SCF, IL3 and erythropoietin.

The amount of growth factors used in the cultures depends on the activity of the factor preparation and on the combination of growth factors used. Typically, concentrations range from 0.5 to 500 ng/ml. The optimum concentration of each growth factor has to be determined for individual culture conditions since some growth factors act synergistically with other growth factors.

In a preferred embodiment the culture medium used in step b) is the same as the one used in step a). Preferably, the growth factors used in step b) are the same as those used in step a), however this is not compulsory.

The culture medium in step b) preferably comprises erythropoietin. Preferably erythropoietin is the only growth factor used in step b). The interest of step b) depends upon the differentiation stage of the cells obtained from step a). EPO indeed favors proliferation of progenitors present in the cultured cells.

Erythropoietin is then removed for subsequent step c). In step c), the cells are cultured substantially in the absence of EPO. Removal of EPO accelerates terminal differentiation. Preferably in step c) the cells are cultured in the absence of any haematopoietic growth factor, most preferably in the absence of any growth factor.

The Supporting Cells

In step c) or b) of the protocol, the cells are contacted with supporting cells.

This step can be performed with the cells adhering to a solid support or being in suspension.

The purpose of these supporting cells is to mimic the native marrow microenvironment, that is formed of cells that support the growth of the haematopoietic stem cells (Lichtman, 1981).

In the context of the invention, the supporting cells are cells that in vitro support the growth of the haematopoietic stem cells and their maturation into enucleated erythrocytes.

These supporting cells can originate from embryo, fetus or any conjunctive tissue.

Preferably, they originate from a marrow microenvironment.

In particular, the method of the present invention makes use of a preparation obtained from the native marrow microenvironment, or of a reconstituted marrow microenvironment.

In a preferred embodiment, the supporting cells are stromal cells, or mesenchymal cells, as described in WO 99/64566.

The stromal cells are preferably derived from bone marrow cells or embryonic yolk sac cells.

Murine stromal cells or mesenchymal stem cells may be used for this purpose. However, primate and other mammalian cells, e.g. human stromal or mesenchymal cells, are suitable as well.

The term "stromal cells" refers to the non-haematopoietic cells of the bone marrow, as well as the macrophages.

Stromal cells include endothelial cells, nonstriated vascular cells (fibroblastic cells), adipocytes and macrophages.

Stromal cells derive from mesenchymal stem cells.

Accordingly, any process that is useful to recover mesenchymal stem cells (MSC) or stromal cells from mammalian, e.g. human tissue may be utilized to result in a population of cells comprising mostly mesenchymal stem cells or stromal cells. In one aspect, the method of isolating human mesenchymal stem cells or stromal cells comprises the steps of providing a tissue specimen containing mesenchymal stem cells or stromal cells, preferably bone marrow; isolating the mesenchymal stem cells or stromal cells from the specimen, for example, by density gradient centrifugation; adding the isolated cells to a medium which contains factors that stimulate mesenchymal stem cells or stromal cell growth without differentiation, and allows for the selective adherence of only the mesenchymal stem cells or stromal cells to a substrate surface in culture; culturing the specimen-medium mixture; and removing the non-adherent matter from the substrate surface, resulting in an isolated population of mesenchymal stem cells or stromal cells.

In direct enrichment of MSC has been described in particular in Pittenger, 1999. Various other particular methods for purifying MSC have been described. They can be selected by enrichment of cells expressing a specific membrane marker, such as CD49a (Deschaseaux, 2000) and Stro1 (Simmons, 1991).

Negative selection can also be contemplated, based on negative selection of CD45 and GlycoA markers (Reyes, 2001).

In a particular embodiment, the supporting cells are genetically modified cells, e.g. supporting cells that express an exogenous gene coding for a growth factor and a factor promoting attachment of the cells.

Preferably the supporting cells and the cells obtained from step a) are co-cultured in step c) and optionally b) under appropriate culture conditions such that the supporting cells adhere or not to a substrate surface. The supporting cells are plated at a density in a range from 200 to $5.10^5$ per $cm^2$, preferably from $10^3$ to about $10^5$ cells per $cm^2$.

Preferably, in the case where the supporting cells adhere to a surface, the supporting cells are used for the co-culture when they reach confluence. Usually the confluence is reached from 20,000 to about 80,000 cells per $cm^2$ and in a preferred embodiment, the confluence is reached around 40,000 cells per $cm^2$. The haematopoietic stem cells (HSC) are thus preferably at a cell density in a range from about 200 to about 40,000 cells per $cm^2$. The cells obtained from the step a) are preferably at a cell density in a range from about $10^3$ to about $2\times10^6$ cells per $cm^2$.

If the supporting cells do not adhere to a substrate surface and are in liquid suspension, the supporting cells are generally suspended at a concentration in a range from 20,000 to about $2.5\times10^6$ cells per milliliter. The haematopoietic stem cells may be suspended at a density range from $10^3$ to about $2\times10^5$ cells per milliliter and the cells obtained from step a) are suspended at a density range from 5,000 to about $10^7$ cells per milliliter.

In the absence of supporting cells, e.g. a microenvironment and in the presence of growth factors alone, the inventors observed that practically no terminal maturation, i.e. enucleation, was achieved.

The Protocol

The time period in which the number of hematopoietic cells are increased is, at least in part, a function of the cell type and on the specific culture vessel used. Routine procedures known to those of ordinary skill in the art can be used to determine the number of cells in culture as a function of increasing incubation time of the cultured cells. Typically, expansion (increase in cell number) is measured by counting the cell numbers by, for example, measuring incorporation of a specific dye or determining the hematocrit, using a hematocytometer or cell counter. Thus, the length of cell culture incubation period varies and depends on the degree of desired expansion.

In general, expansion in liquid cultures is evaluated by the increase in total number of cells from the start of incubation and/or by determining the % $CD34^+$ cells in the culture.

Step a) may last between about 6 to about 15 days or even longer, e.g. to about 28 days. Step c) may last between about 2 to about 14 days.

When the method comprises three steps a), b), and c), the duration of the steps may be approximately as follows:

Approximately step a) lasts between 6 and 10 or 11 days, preferably about 8 days. Step b) may last between 2 and 5 days, preferably about 3 days. Step c) lasts between 2 and 14 days.

When the method comprises two steps a) and c), and step b) is avoided, the duration of the steps may be approximately as follows:

Approximately, step a) lasts between 7 and 15 days, preferably about 11 days. Step c) lasts between 2 and 14 days.

In any embodiment of the invention, the culture step c) is performed until reticulocytes are obtained. This generally occurs after 4 days of culture step c). One may prefer to wait until mature red blood cells are obtained. If so, step c) is performed until mature red blood cells are obtained, which generally occurs after 7 days of culture step c).

After expansion, the cells are harvested and are washed, and preferably filtrated to remove leukocytes, before infusion to the patient.

In a particular embodiment the method of the invention comprises the steps of:

a) culturing haematopoietic stem cells in a culture medium that comprises SCF, IL-3, and erythropoietin (EPO) during 8 days, optionally followed by 3 supplementary days of culture in a medium that comprises SCF and EPO;

b) culturing the cells obtained in step a), in a culture medium that comprises EPO, optionally still in the same culture medium, and in contact with a stromal cell line, during 3 days;

c) culturing the cells obtained in step b), still in contact with the stromal cell line, in the absence of any growth factor, during 4 days, whereby reticulocytes are obtained, or during 7 days whereby mature red cells are obtained.

The method of the invention allows for the massive production of a homogenous population of enucleated erythrocytes.

The potential cell yields are compatible with the clinical requirements for transfusion. A standard RBC concentrate contains about $2 \times 10^{12}$ cells. A cord blood unit contains 2-5× $10^6$ CD34+ cells and a leukapheresis after mobilization with a growth factor like G-CSF normally provides 4-8×$10^6$ CD34+ cells per Kg of body weight, while the levels of amplification are respectively of the order of $10^5$ and $3 \times 10^4$ fold, or even of the order of $10^6$ and $1 \times 10^5$ fold (in the case where the duration of the step a) is 11 days) with an enucleation rate range from about 65% to about 95%. Taking into account all the previous parameters, it is clearly the equivalent of several RBC concentrates which can be produced in this way from a single donation.

Apart from the interest for transfusion in terms of supply and infectious safety—the method makes it possible to easily produce several units derived from one donor and/or autologous transfusion patient—, the method of the invention is also advantageous with regard to transfusion efficacy. It allows the infusion of a cell population homogeneous in age with a life span close to 120 days, whereas the mean half-life of the RBCs obtained from a donor is 28 days due to the simultaneous presence of cells of variable age. This would reduce the number of transfusions that are needed.

The invention is further illustrated by the following examples and figures, which do not limit the scope of the invention.

EXAMPLES

Example 1

Production of Mature RBCs using Murine Cell Line MS5 as Marrow Environment

Materials and Methods

Cell Culture

Normal Bone Marrow (BM), normal Peripheral Blood mobilized with G-CSF [Leukapheresis (LK)] or not (PB) and umbilical Cord Blood (CB) from normal full-term deliveries were obtained with informed consent. CD34+ cells were isolated by supermagnetic microbead selection using Mini-MACS columns (Miltenyi Biotech, Bergisch Glodbach, Germany) (purity >94±3%).

A. Cells were cultured in a modified serum-free medium (Kobari et al., 2000; Giarratana et al., 2000) supplemented with 1% deionized Bovine Serum Albumin (BSA), 120 µg/ml iron-saturated human transferrin, 900 ng/ml ferrous sulfate, 90 ng/ml ferric nitrate and 10 µg/ml insulin (all from Sigma, France).

Another example of cell culture medium is Iscove modified Dulbecco's medium (IMDM, Biochrom, ref F0465). The table below (Table 1) is an example of all the components for 100 ml of medium.

TABLE 1

| Component | Supplier, storage | Vol. of stock solution (ml) | Final concentration |
|---|---|---|---|
| IMDM without glutamine | Biochrom, +4° C. | QSP 100 ml | — |
| L-glutamine 200 mM | Life Technologies, −20° C. | 2 | 2 mM |
| Penicillin and streptomycin | Life Technologies, −20° C. | 1 | 1% vol/vol |
| Inositol at 4 mg/ml in sIMDM | Sigma | 1 | 40 µg/ml |
| Folic acid at 1 mg/ml in IMDM | Sigma | 1 | 10 µg/ml |
| Monothioglycerol at 0.16 M in IMDM | Sigma, +4° C. | 0.1 | $1.6 \times 10^{-4}$ M |
| Fransferrin at 15 mg/ml | Sigma, +4° C. | 0.80 | 120 µg/ml |
| Insulin at 1 mg/ml in 5 mM HCl | Sigma, −20° C. | 1 | 10 µg/ml |
| Ferrous nitrate (FN) at 0.018 mg/ml | Sigma | 0.5 | 90 ng/ml |
| Ferrous sulfate (FS) at 0.18 mg/ml | Sigma | 0.5 | 900 ng/ml |
| BSA (10% i.e. 100 mg/ml) | Stem Cell Technologies, −20° C. | 10 | 10 mg/ml |
| Or HSA (LFB, 20% i.e. 200 mg/ml) | LFB, Vialebrex, +4° C. | 5 | 10 mg/ml |

The expansion procedure comprised three steps.

In the first step (days 0-8), $10^4$/ml CD34+ cells were cultured in the presence of $10^{-6}$ M hydrocortisone (OHC) (Sigma), 100 ng/ml Stem Cell Factor (SCF, Amgen, Thousand Oaks, Calif., USA), 5 ng/ml IL3 (R&D Systems, Abingdon, UK) and 3 IU/ml Epo (Eprex, Janssen-Cilag, Issy-les-Moulineaux, France). On day 4, one volume of cell culture was diluted in four volumes of fresh medium containing OHC, SCF, IL3 and Epo.

In the second step (days 8-11), the cells were resuspended at $5 \times 10^4$, $10^5$, $2 \times 10^5$ or $3 \times 10^5$/ml (for CB, LK, BM and PB cells respectively) and co-cultured on an MS-5 stroma cell line in fresh medium supplemented with Epo.

In the third step (from day 11), the cells were cultured on stromal cells (MS5) in fresh medium without cytokines. The cultures were maintained at 37° C. in 5% $CO_2$ in air. If the culture is maintained for more 15 days (for protocol A) from their initiation, the cells are preferably washed, resuspended at $5-6 \times 10^6$/ml and co-cultured on a new stromal layer. During this step of culture, addition of 5-20% human AB serum to the medium allows preservation of the cultured red blood cells (cRBCs). Cells were stained with May-Grünwald-Giemsa reagent for morphological analyses, while enucleated cells were monitored for standard hematological variables including the MCV (fL), MCHC (%) and MCH (pg/cell) using an XE2100 automat (Sysmex, Roche Diagnostics, Basel, Switzerland).

B. An alternative protocol was used, which comprises the steps of:

First step: prolonging the already described first step of culture (protocol A) by 3 days (until day 11). In this case, cells from day 8 were harvested, washed and resuspended at $5 \times 10^4$, $10^5$, $2 \times 10^5$ or $3 \times 10^5$/ml (for CB, LK, BM and PB cells respectively) in fresh medium containing SCF and Epo.

Second step: delaying of three days the already described second step of culture (protocole A) usually from day 11 to day 14: cells (usually from day 11 from protocole B instead of day 8 from protocole A) were resuspended at $10^5$, $2 \times 10^5$, $3-4 \times 10^5$ or $4-6 \times 10^5$/ml (for CB, LK, BM and PB cells respectively) and co-cultured on the MS-5 stromal cell line in fresh medium supplemented with Epo. The cells were usually washed at day 14 to remove factors and metabolites.

Third step: delaying of four days the already described third step of culture (protocole A) usually from day 14 to day 18. If the culture is maintained for more 18 days (for protocol B) from their initiation, the cells are preferably washed, resuspended at $5-6 \times 10^6$/ml and co-cultured on a new stromal layer. During this step of culture, addition of 5-20% human AB serum to the medium allows preservation of the cultured red blood cells (cRBCs).

Further details are given below as an example of ingredients that can be used (see Table 1):

Penicillin and Streptomycin: the stock solution is a mixture of penicillin at 5000 U/ml and streptomycin at 5000 µg/ml.

Inositol: 20 mg of powdered inositol (kept at room temperature) can be dissolved in 5 ml of IMDM and may be stored for up to one week at 4° C.

Folic acid: 20 mg of powdered folic acid (kept at room temperature) can be dissolved in 20 ml of pre-warmed IMDM and may be stored for one week at 4° C. It is better to have a pre-warmed solution prior to use.

Monothioglycerol: 10 µl of an 11.56 M stock solution (Sigma, 11.56 M, d=1.25, 98% purity, MW=108.16) can be dissolved in 712 µl of IMDM. A 0.16 M solution of monothioglycerol is obtained.

Holo-transferrin: holo-transferrin (Sigma), saturated with 1200 to 1600 µg of iron per gram of transferrin, can be dissolved at 15 mg/ml in a solution of NaCl-150 mM, $Na_2HPO_4$ 0.8 mM, $NaH_2PO_4$ 0.2 mM, pH 7.5; to 10 ml of this solution, 340 µl of a solution $FeCl_3$ 10 mM in 1 mM HCl was added. The solution can be filtered sterilized (0.2 µm) and stored at 4° C.

Insulin: Powdered insulin (stored at −20° C.) can be dissolved at 1 mg/ml in 5 mM HCl. The solution can be stored at −20° C.

Ferrous nitrate: ferrous nitrate powder can be initially dissolved in distilled water at 1.8 mg/ml to avoid formation of salt complexes. This first solution can be diluted 1/100 in IMDM (secondary solution at 0.018 mg/ml) and can be stored at 4° C.

Ferrous sulfate: ferrous sulfate can be initially dissolved in distilled water at 18 mg/ml in order to avoid formation of salt complexes. This first solution can be then diluted 1/100 in IMDM (secondary solution at 0.18 mg/ml) and may be stored at 4° C.

Hydrocortisone: Hydrocortisone (OHC) can be added during the first step of culture ($10^{-6}$ M final concentration). 20 mg of hydrocortisone salt (Sigma ref H2270, MW=484.5, stored at −20° C.) can be dissolved in 4.12 ml of IMDM and then diluted 1/100 in the same medium to give a $10^{-4}$ M solution, which can be filtered through a 0.22 µm filter and may be stored at +4° C. for one week. 1 ml of $10^{-4}$ M OHC solution to 100 ml of final culture medium.

Stromal Cells

MS-5 can be used as adherent layer.

The MS-5 stromal cell line is expanded in αMEM medium containing ribonucleosides and deoxyribonucleosides and Glutamax (Invitrogen, ref 32571-028) and supplemented with 10% fetal calf serum (FCS).

After confluence, adherent cells are collected after 7-10 minutes treatment by trypsin-EDTA 1× (Invitrogen, ref 25300-54) at 37° C. $10^6$ cells/cm² are usually recovered. Cell detachment is controlled under inverted microscope. Reaction is stopped by adding 0.5 ml FCS/25 cm² flask. Cells are washed and replated at 4000 cells/cm² in αMEM+glutamax+10% FCS medium. Cells are incubated at 37° C. under 5% $CO_2$. Adherence is usually reached after one week.

Usually, for co-culture with erythroid cells, MS-5 may be used up to two weeks after trypsin treatment.

Semisolid Culture Assays

BFU-E, CFU-E and CFU-GM progenitors were assayed as previously described in Giarratana, M. C. et al. (1998), in methyl cellulose cultures incubated at 37° C. in 5% $CO_2$ in air.

Flow Cytometry

Cells were labeled with unconjugated or fluorescein isothiocyanate (FITC)- or phycoerythrin (PE)-conjugated antibodies. Antibodies to CD71 (Dako, Carpinteria, Calif.) and to CD45 and CD34 (Immunotech, Marseilles, France) were used for phenotyping and cells were stained with the vital nucleic acid dye LDS-751. Analyses were performed on a FACSCalibur flow cytometer (Becton Dickinson) using Cell Quest software.

Deformability Measurements

The reticulocytes obtained on day 15 of culture were separated from nucleated cells by passage through a deleukocyting filter (Leucolab LCG2, Macopharma, Tourcoing, France) and the enucleated cells were examined by ektacytometry, a laser diffraction method. In the ektacytometer (Technicon, Bayer Corp.), cells suspended in 4% polyvinylpyrrolidone solution are exposed to an increasing osmotic gradient (from 60 to 450 mosM) and the change in their laser diffraction pattern is recorded. The photometric measurement produces a signal termed the deformability index (DI). Analysis of the DI curve provides a measure of the dynamic deformability of the cell membrane as a function of the osmolality at a constant applied shear stress of 170 dynes/cm$^2$. The DI max, quantified as the maximum value of the DI normally attained at a physiologically relevant osmolality, is related to the mean surface area of red cells.

Glucose-6-Phosphate Dehydrogenase and Pyruvate Kinase Activities

Digitonin (0.2%) was added to erythrocytes obtained after leukocyte depletion and hemoglobin was quantified by spectrophotometry using Drabkin's reagent. G6PD and PK activities were determined by measurement of the rate of increase in NADPH absorbance at 340 nm (Beutler et al. (1977) using a Synchron CX4 Beckman spectrometer and reagents from Randox Laboratories (Crumlin, UK) and Roche Diagnostics, respectively. Results were expressed in units per gram of hemoglobin.

Hemoglobin Analyses

The percentage of the various Hb fractions was measured by CE-HPLC using a Bio-Rad Variant II Hb analyser (Bio-Rad Laboratories, Hercules, Calif., USA). Globin chain composition was determined by RP-HPLC as previously described (Pic, Ducrocq et al., 1994; Papassotiriou, Ducrocq et al., 1998).

Functional Properties

The methemoglobin fraction was determined spectrophotometrically in the near UV region (350 to 450 nm). Samples were equilibrated under pure CO and a final concentration of 200 µM potassium cyanide was added to the buffered solution of hemoglobin. The total heme concentration for normalization was calculated from the maximum absorption of the CO spectrum at 420 nm after addition of 200 µM potassium dithionite.

The binding properties of hemoglobin were studied by flash photolysis in a 1 mm optical cuvette. Briefly, the kinetics of the rebinding of CO to intracellular hemoglobin tetramers were analyzed at 436 nm after photolysis with a 10-ns pulse at 532 nm as described previously in Marden et al., (1988).

Validation in the NOD/SCID Mouse Model

All experiments and procedures conformed to the French Ministry of Agriculture regulations for animal experimentation (1987). NOD/SCID-LtSz-scid/scid (NOD/SCID) mice were raised under sterile conditions. Before cell injection, mice 6 to 8 weeks old were sublethally irradiated with 2.5 Grays from a $^{137}$Cs source (2.115 Gy/min). In order to saturate the reticulo-endothelial system, human type 0 RBCs were injected intraperitoneally (i.p., 4-5×10$^9$ cells per mouse). After 24 hours, the mice were injected i.p. with in vitro generated RBCs from day 19 cultures (4-5×10$^9$ cells per mouse) which had been washed and labeled with CFSE (Lyons et al., (1994)). Controls received heparinized peripheral blood under the same conditions. Three animals were used in each experimental group. The human RBC clearance was determined by following the CFSE-labeled cells by flow cytometry in 5 µl samples of heparinized blood drawn from each mouse at various times by retro-orbital vein puncture. In each group, a regression line was established from the percentage of CFSE-labeled cells in murine blood.

Results

Massive amplification of erythroid cells: Cells were amplified in a well-defined serum-free medium, in the presence of a combination of growth factors and in co-culture on the murine stromal cell line MS5, which reproduced ex vivo a microenvironment mimicking that existing in vivo (Suzuki, 1992). It was possible to obtain by day 15 a plateau of the mean cell amplification of 16,500 fold (9,200 to 25,500) for CD34$^+$ cells from Bone Marrow (BM) or Peripheral Blood (PB), of 31,200 fold (23,700 to 34,000) for those obtained by leukapheresis after mobilization with G-CSF and of 140,000 fold (93,000 to 277,000) for those derived from Cord Blood (FIG. 1A).

Figure 1B:
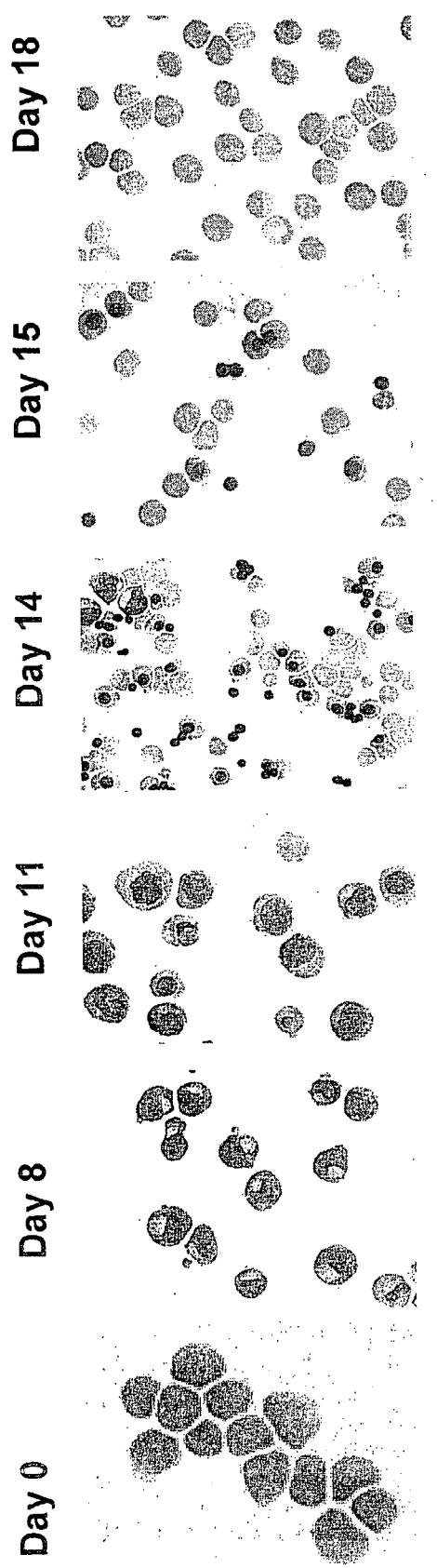

A commitment to the erythroid lineage was morphologically evident by day 8 (95 to 98% of erythroblasts). The subsequent terminal differentiation was rapid as the percentage of enucleated cells was 1-5% on day 11 and 65-80% on day 15 (FIG. 1B). At this stage, 98±1% of the cells were reticulocytes (FIG. 2B) with a Mean Cell Volume (MCV) of 130±5µ$^3$, a Mean Corpuscular Hemoglobin Concentration (MCHC) of 18±1% and a Mean Cell Hemoglobin (MCH) of 23±−1 pg.

Figure 1C:
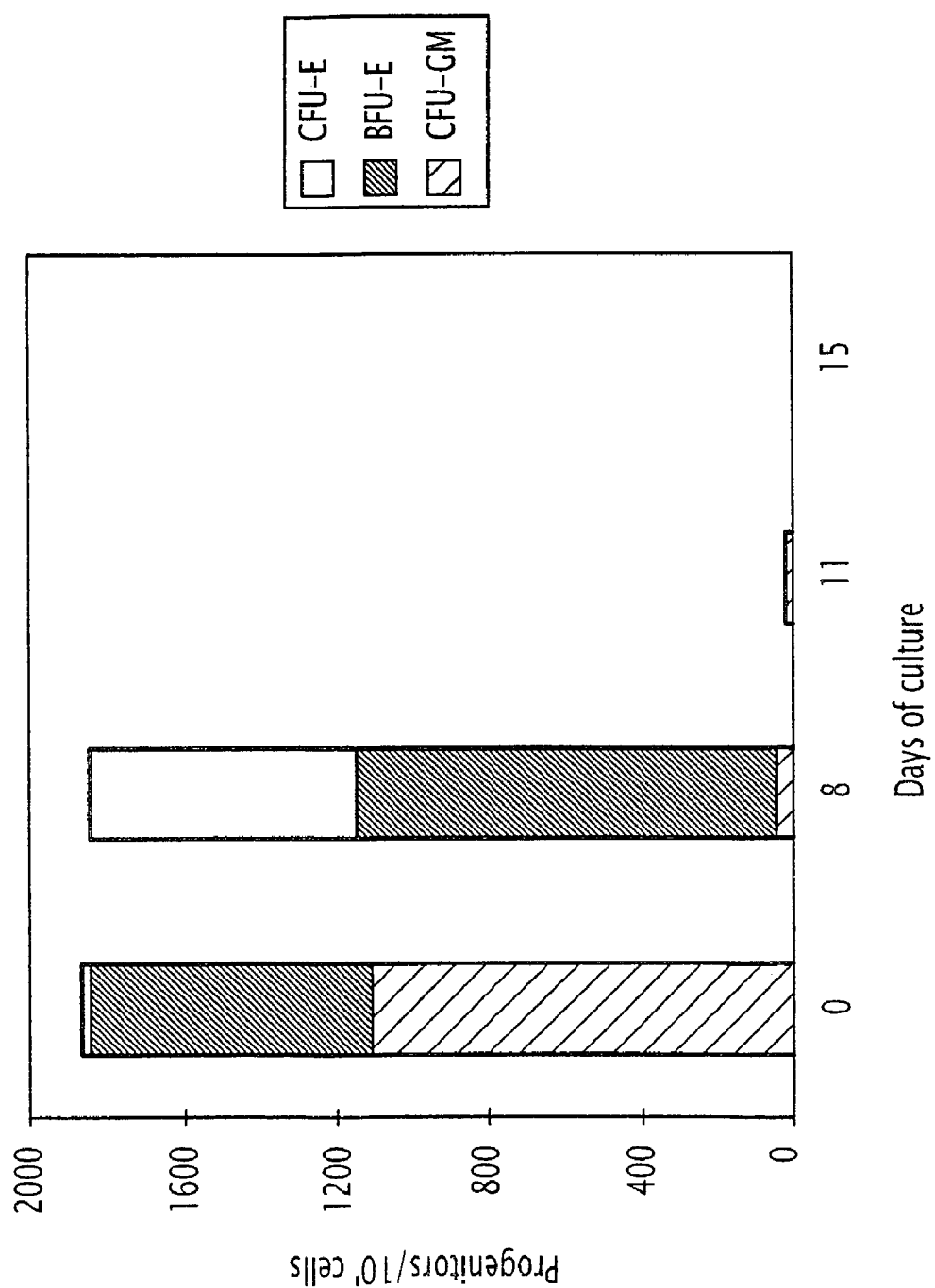
Figure 2A:
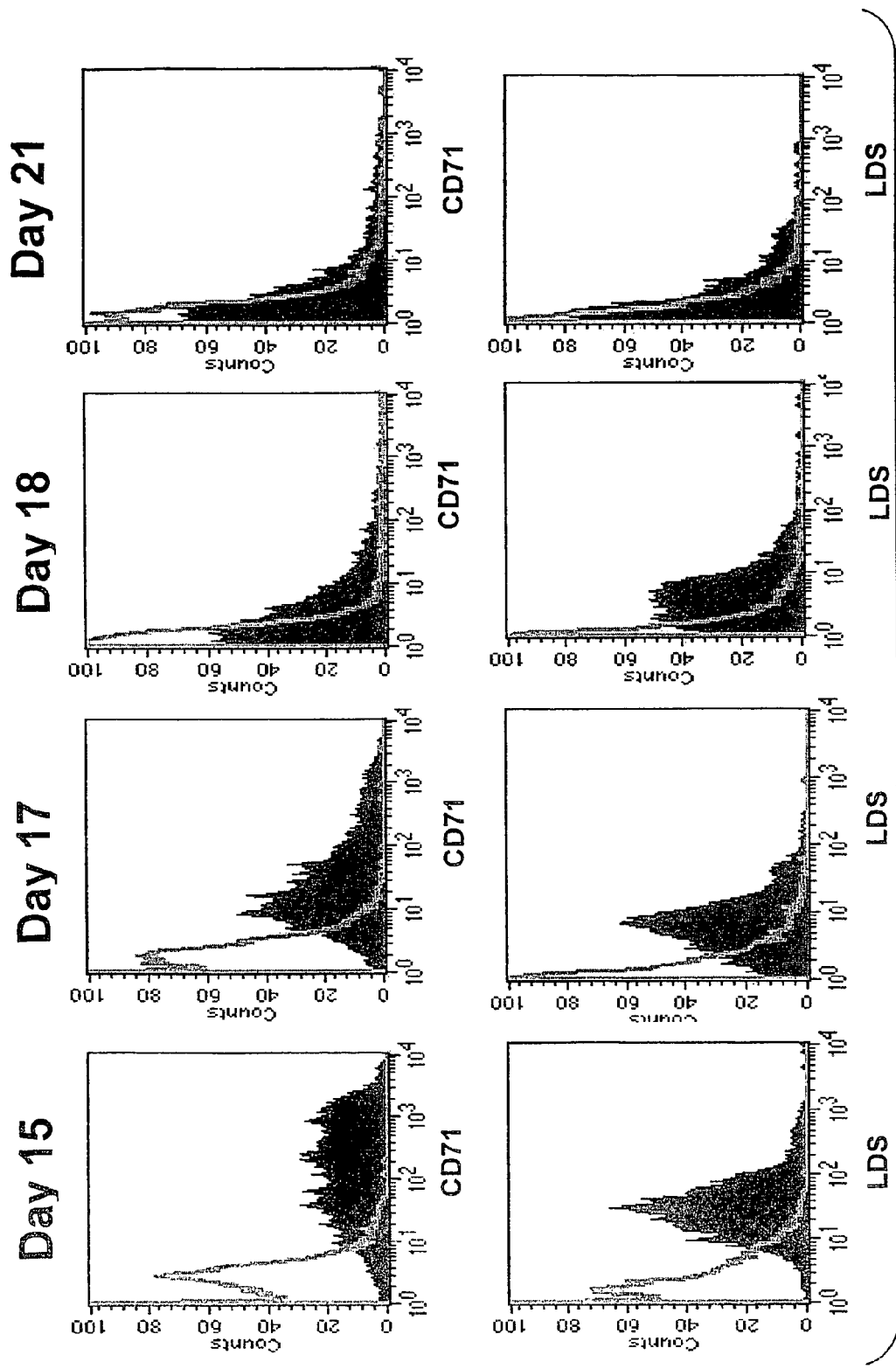
FIG. 2: Maturation of reticulocytes into RBCs. (A) FACS analyses of expression of the transferrin receptor (CD71) and staining with laser dye styryl (LDS) from day 15 to day 18 in one representative experiment using samples from a BM culture. Open histograms: negative control. Solid histograms: cells stained by LDS or an anti-CD71 antibody. (B) Photographs of reticulocytes stained with Cresyl Brilliant Blue on days 15 and 18 (magnification×500). On day 15, 65% of the cells were enucleated, 98% of which were reticulocytes. On day 18, 100% of the cells were enucleated and 82% were RBCs.
Figure 2B:
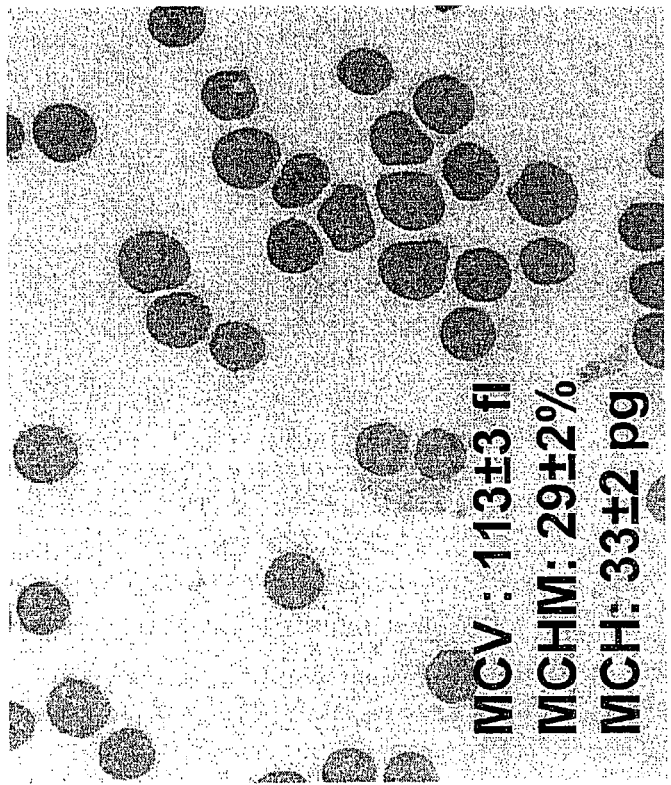
Figure 2B:
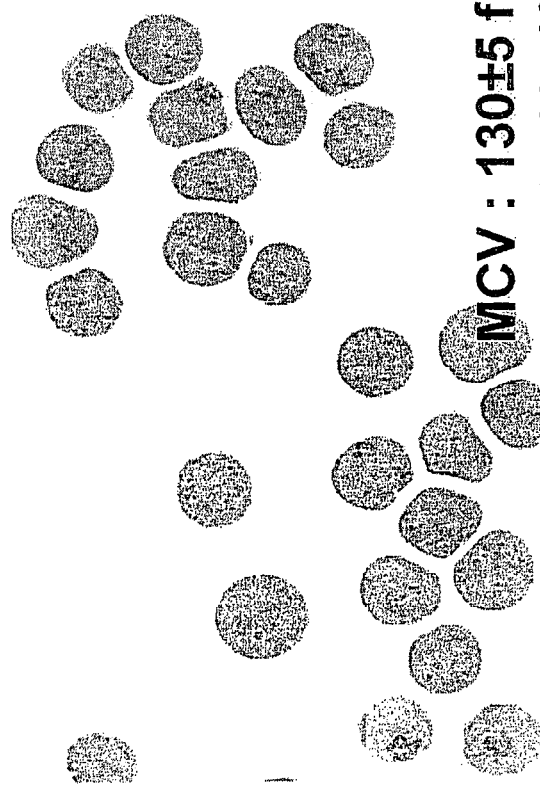
Figure 3:
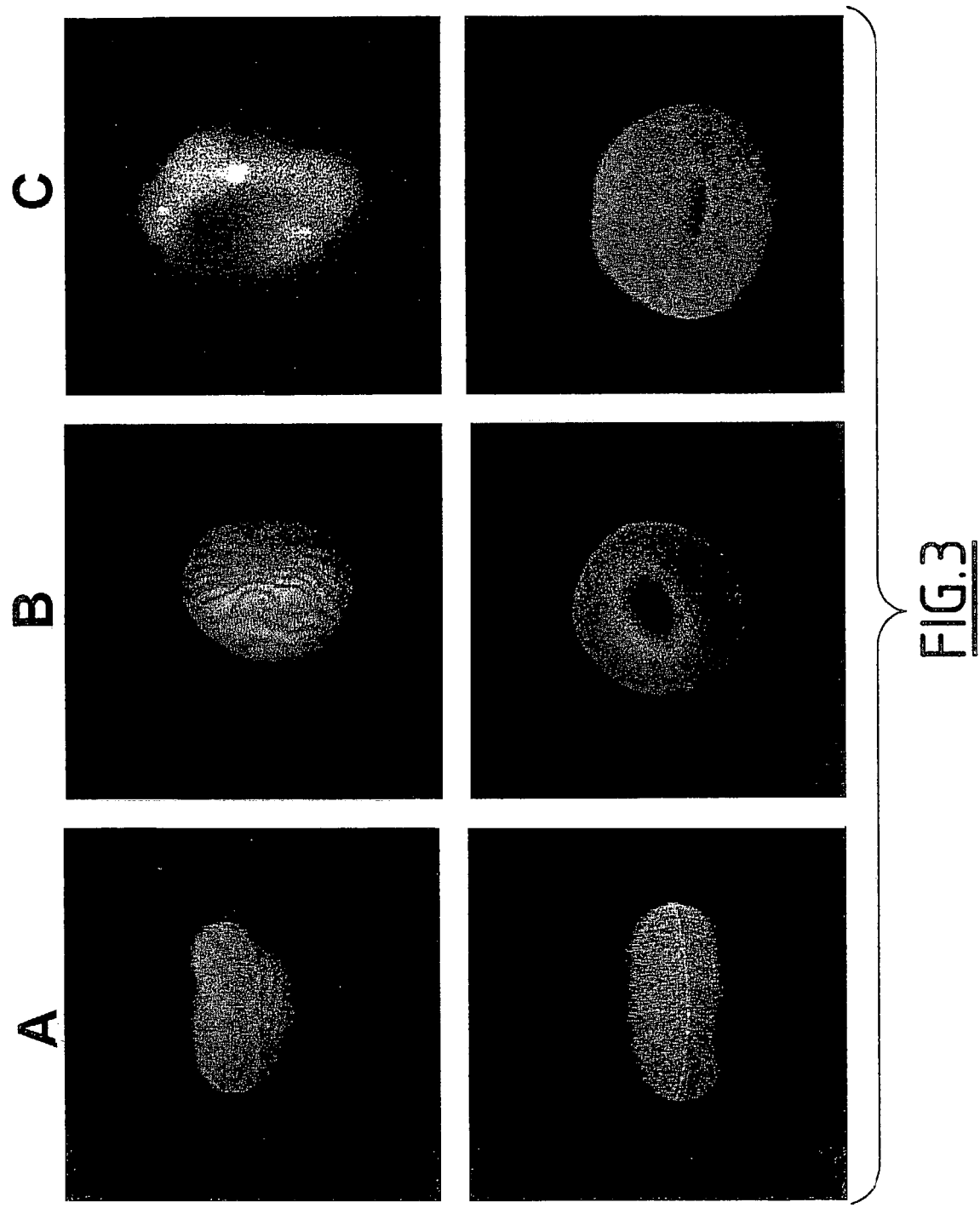
FIG. 3: Confocal microscopy images. Enucleated cells generated in vitro were labeled with CFSE (Carboxyfluorescein diacetate Succinimidyl Ester, which forms covalent links with intracellular macromolecules) and analyzed by confocal laser scanning microscopy (magnification×400). Different stages of maturation are shown. Top line: an immature reticulocyte with a characteristic ruffled appearance. Middle line: a mature reticulocyte, a cup-shaped cell. Bottom line: a mature red cell, close to a biconcave disc. Views are: profile (A), front (B) and side (C).

Differentiation of the reticulocytes into mature RBCs continued from day 15 to day 18, as shown by the disappearance of nucleic material and by the progressive loss of expression of the transferrin receptor CD71 and staining with Laser Dye Styryl (LDS). At this stage, 90 to 100% of the cells were enucleated (FIG. 2A). These erythrocytes displayed characteristics close to those of native RBCs, namely an MCV of 113±3 fL, an MCH of 33±2 pg and an MCHC of 29±2%. The cell yield on day 18 with respect to day 15 was 77±5% with a mean reticulocyte content of 18±4%. Distinct morphologic stages of the maturation as viewed by confocal microscopy are shown in FIG. 3. This massive differentiation of pure erythroid cells can undoubtedly be attributed to the targeted induction of the proliferation of erythroid progenitors (BFU-E and CFU-E), to the detriment of granulo-macrophagic progenitors (CFU-GM) which all disappeared rapidly between days 8 and 11 (FIG. 1C).

These culture conditions therefore permitted (i) during the first 8 day phase in a liquid medium, triggering of a strong proliferation of primitive HSCs in the presence of SCF and IL3 and targeted induction by Epo of an exclusively erythroid differentiation, (ii) during the second 3 day phase, initiation of terminal maturation through the combined effect of the microenvironment and the single growth factor Epo with maintenance of the high level of proliferation and (iii) completion of cell differentiation and terminal enucleation in the presence of the microenvironment alone.

Functional Reticulocytes and Red Blood Cells

Figure 4:
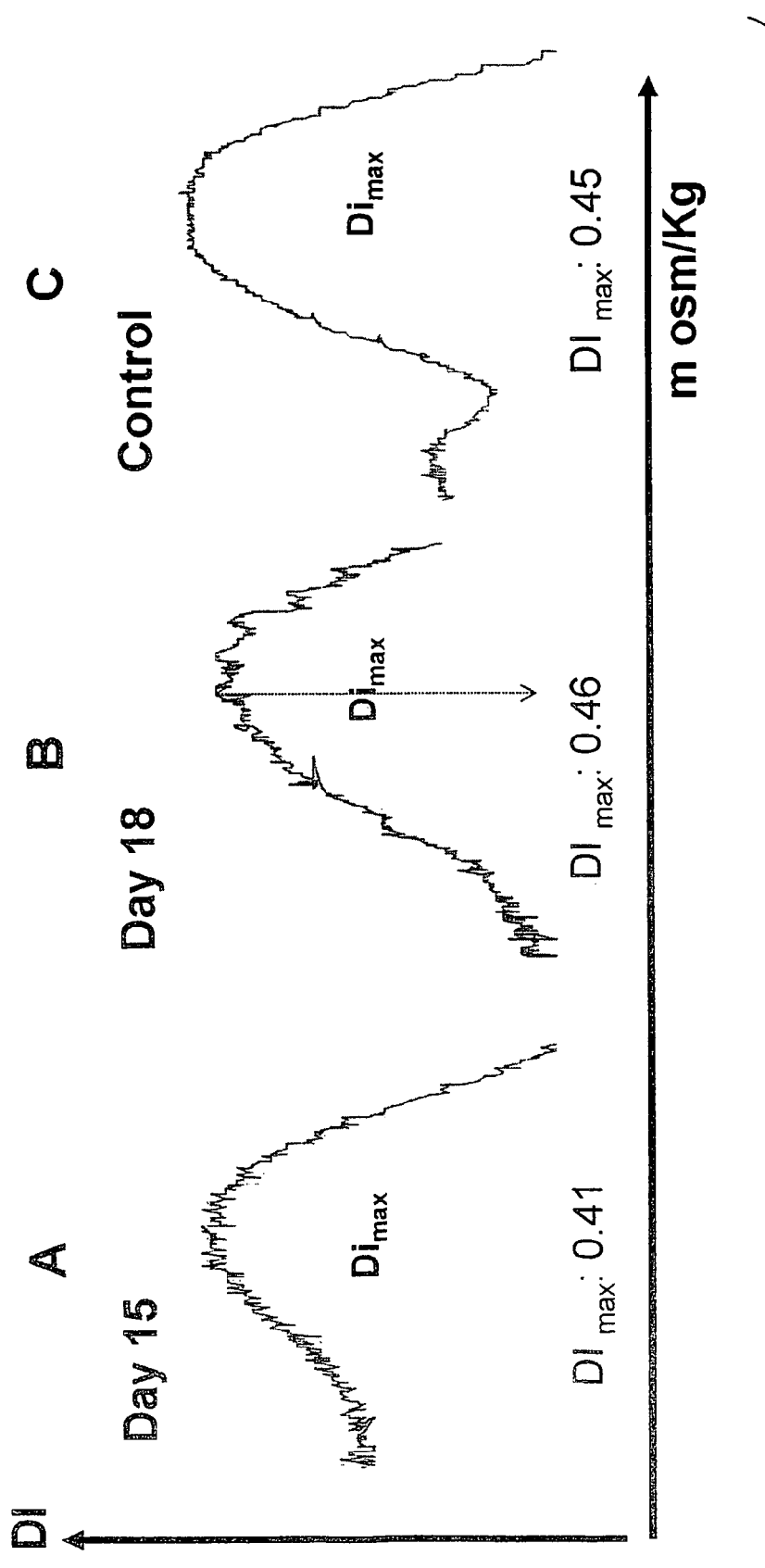
FIG. 4. Deformability profiles. Ektacytometry in an osmolar gradient was used to measure the elongation of enucleated erythrocytes by flow cytometry. The curves define a maximum Index of Deformation (ID max) in an iso-osmolar medium. The ID max lay within the same range as the control (0.41 to 0.53) for all the cell types analyzed, indicating an equal capacity for deformation. Representative curves for (A) reticulocytes derived from SC progenitors and (B) RBCs derived from SC progenitors, as compared to native RBCs (C).

The reticulocytes and RBCs generated ex vivo had a Glucose-6-Phosphate Dehydrogenase (G6PD) content of 42±1.4 units and a Pyruvate Kinase (PK) content of 83±1.8 units per gram of hemoglobin, consistent with the homogeneous nature and young age of the cell populations produced (Jansen et al., 1985). This indicated that they were capable of reducing glutathion and maintaining ATP levels and thus of avoiding the accumulation of 2,3-Diphosphoglycerate (2,3-DPG), which would decrease the affinity of hemoglobin. The deformability of these reticulocytes and RBCs, as evaluated by ektacytometry, was comparable to that of native erythrocytes (FIG. 4) (Cynober et al., 1996).

Figure 5:
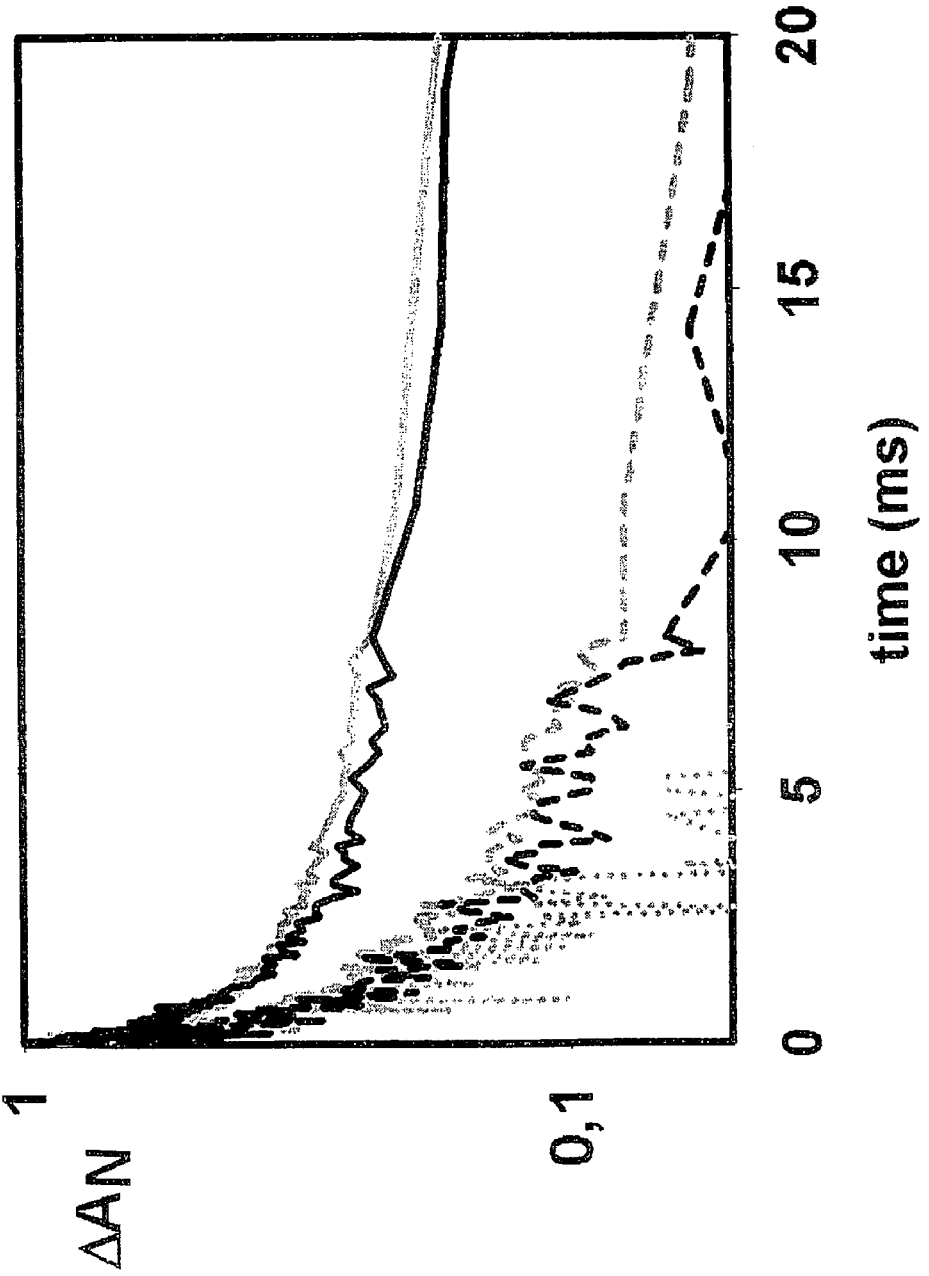
FIG. 5: CO rebinding kinetics of hemoglobin. CO rebinding after flash photolysis of the hemoglobin content of ex vivo generated RBCs from day 18 cultures (grey curves), as compared to that of hemoglobin from a fresh RBC suspension (black curves). The two samples show similar binding and allosteric properties. As the photodissociation yield decreases, the slow CO rebinding phase diminishes due to the presence of T-state molecules.

The functionality of the hemoglobin of the RBCs generated in vitro was studied by flash photolysis. Cooperation between the different subunits was observed, confirming an allosteric behavior characteristic of tetrameric hemoglobin. This molecule was able to fix and release oxygen (FIG. 5) as would be expected for native hemoglobin. Methaemoglobin (Met-Hb) was not detected in the analyzed samples. This suggested that the cRBC were enzymatically capable of reversing Hb oxidation.

In Vivo Fate of Cultured Human RBCs

Figure 6:
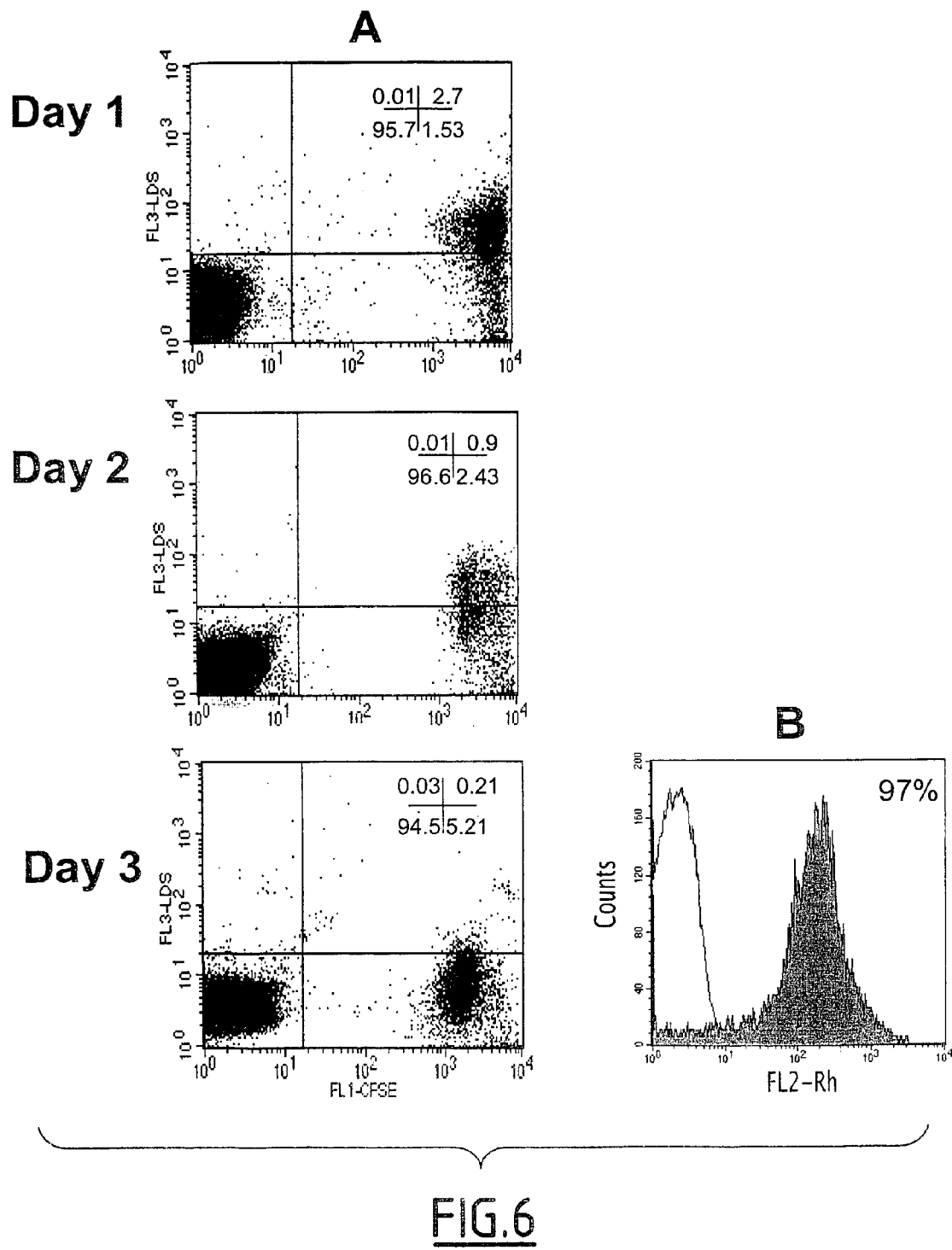
FIG. 6: Follow up of the CFSE-labelled cRBC in the NOD/SCID mouse model by flow cytometry. One representative experiment is shown. (A): kinetics of expression of CFSE/LDS markers in cells from peripheral blood of the NOD/SCID mice. Horizontal axis, CFSE detection; vertical axis, detection of LDS. Quadrant statistics are precised in each dot plot. (B) At day 3, cells were co-labelled with PE-anti-Rh D antibody (solid histogram) or its control isotype (open histogram). Results are expressed in terms of Rh percentage within the CFSE$^+$ cells.

In order to follow their in vivo evolution CFSE-labelled-reticulocytes generated from leukapheresis were injected intraperitoneally into NOD-SCID mice. After infusion, cRBCs persisted in the circulation to the same extent as native RBCs: CFSE$^+$ cells were detected during 3 days in both groups of transfused animals. In vivo, the transfused reticulocytes fully matured into RBCs as shown by the appearance of CFSE$^+$/LDS$^-$ cells (FIG. 6): 36%, 73% and 96% were mature RBCs at day 1, 2 and 3 respectively which is in concordance with the results obtained in vitro. RhD antigen surface expression confirmed the human origin of CFSE$^+$ cells.

Impact of the Ex Vivo Microenvironment on the Terminal Maturation of Erythroid Cells In the absence of a microenvironment and in the presence of growth factors alone, the cell proliferation and erythroid differentiation capacities were not altered ($5.6 \times 10^5$ fold amplification on day 15 with 99% erythroid cells). However, practically no terminal maturation, i.e. enucleation, was achieved (2±1%). Thus, placing a transwell of 0.45 μm between the adherent and non adherent cells prevented all enucleation and induced a secondary cell lysis.

Moreover, the kinetics of production of erythroid progenitors (CFU-E, BFU-E) confirmed that an absence of stroma does not favor terminal differentiation, since on day 11 numbers of these progenitors were 20 to 700 times greater than in co-culture on MS5 cells.

Study of the Synthesis of Hemoglobin

The inventors have observed that the nature of the haemoglobin synthesized depended on both the origin of the CD34$^+$ cells and the culture conditions. cRBC derived from PB or adult BM contained haemoglobin A (HbA) (94±1.7% and 95±0.6% respectively), with a similar modulation of haemoglobin F (HbF) (ratio γA:γG of 53:47 and 52:48 respectively). cRBC obtained from CD34$^+$ cells derived from CB contained essentially foetal haemoglobin (64±13%) with a partial modulation of HbF (mean ratio γA:γG of 59:41), starting from 80±7% of Hb F in the CB samples. These observations reflect the possibility of the occurrence ex vivo of a switch from F cells to non F cells. This ex vivo synthesis of HbF by cRBC is linked to the culture conditions, since in previous work (Neildez-Nguyen et al., 2002) it was found that the erythroblast progenitors/precursors obtained after 10 days of culture in the absence of a microenvironment gave rise in vivo, following injection into NOD/SCID mice, to mature RBCs containing 96% functional HbA with a complete modulation of HbF (ratio γA:γG of 35:65). Stimulation of the expression of HbF in patients with a severe haemoglobinopathy (sickle cell anemia, β-thalassemia . . . ) is an interesting therapeutic approach which could be addressed here ex vivo.

Example 2

Production of Mature RBCs using Mesenchymal Cells as Marrow Environment

The protocol of example 1 was repeated, while replacing the MS5 stroma cell line by mesenchymal stroma cells (MSC, Prockop D. J, 1997).

Selection and Expansion of the Stromal Cells

Mesenchymal Stromal Cells (MSCs) are established from whole normal adult bone marrow.

First step, the selection of mesenchymal stromal cells:

Total cells are plated at 50,000 cells/cm$^2$ in αMEM medium without ribonucleosides and deoxyribonucleosides and with Glutamax (Invitrogen, ref 32561-029 Paisley, Scotland) supplemented with 10% fetal calf serum (FCS)±1 ng/ml βFGF. After 3-5 days the non adherent cells are removed. The adherent cells are fed twice a week until confluence (around 10-20 days). At the end of the first step, one may consider that the stromal cells are highly selected from the whole bone marrow cells thanks to their adherent properties.

Second step, the expansion of mesenchymal stromal cells:

Adherent cells are collected after 5-6 minutes treatment by trypsin-EDTA 1× at room temperature. Cell detachment is controlled under inverted microscope. Reaction is stopped by adding 0.5 ml FCS/25 cm$_2$ flask. Cells are washed and replated at 1000-3000 cells/cm$^2$ in fresh medium supplemented with 10% FCS±βFGF. Cells are fed once or twice a week until confluence. Cells are incubated at 37° C. under 5% CO$_2$ until confluence. Adherent MSCs are expanded and purified through at least two successive passages since the second step.

Cell Culture Results

It was possible to obtain by day 15 a plateau of the mean cell amplification of 13,100 fold (8,000 to 23,000) for CD34$^+$ cells from Bone Marrow (BM) or Peripheral Blood (PB), and of 57,300 fold (32,000 to 73,000) for those derived from Cord Blood (CB)) according to the following protocole: step a) 8 days, step b) 3 days, and step c) 4 days.

The commitment to the erythroid lineage and final maturation into RBCs were strickly similar to those observed on MS-5 layer (Example 1).

REFERENCES

Baum et al. 89 PNAS USA 2804-2808 (1992)

Bessis, M., [Erythroblastic island, functional unity of bone marrow.]. Rev Hematol, 1958. 13(1): p. 8-11

Beutler, E., et al., International Committee for Standardization in Haematology: recommended methods for red-cell enzyme analysis. Br J Haematol, 1977. 35(2): p. 331-40

Cynober, T., N. Mohandas, and G. Tchernia, Red cell abnormalities in hereditary spherocytosis: relevance to diagnosis and understanding of the variable expression of clinical severity. J Lab Clin Med, 1996. 128(3): p. 259-69—Friedenstein A J, 1977, Exp Hematol 2, 83-92.

Deschaseaux F, Cell Physiol 2000, 184, p 319-325

Dolznig, H., et al., Apoptosis protection by the Epo target Bcl-X(L) allows factor-independent differentiation of primary erythroblasts. Curr Biol, 2002. 12(13): p. 1076-85

Fibach, E., et al., Proliferation and maturation of human erythroid progenitors in liquid culture. Blood, 1989. 73(1): p. 100-3

Freyssinier, J. M., et al., Purification, amplification and characterization of a population of human erythroid progenitors. Br J Haematol, 1999. 106(4): p. 912-22

Giarratana, M. C., et al., Presence of primitive lymphoid progenitors with NK or B potential in ex vivo expanded bone marrow cell cultures. Exp Hematol, 2000. 28(1): p. 46-54

Giarratana, M. C. et al. Cell culture bags allow a large extent of ex vivo expansion of LTC-IC and functional mature cells which can subsequently be frozen: interest for a large-scale clinical applications. Bone Marrow Transplant 22, 707-15 (1998).

Hanspal, M. and J. S. Hanspal, The association of erythroblasts with macrophages promotes erythroid proliferation and maturation: a 30-kD heparin-binding protein is involved in this contact. Blood, 1994. 84(10): p. 3494-504.

Hanspal, M., Y. Smockova, and Q. Uong, Molecular identification and functional characterization of a novel protein that mediates the attachment of erythroblasts to macrophages. Blood, 1998. 92(8): p. 2940-50

Jansen, G., et al., Characteristics of hexokinase, pyruvate kinase, and glucose-6-phosphate dehydrogenase during adult and neonatal reticulocyte maturation. Am J Hematol, 1985. 20(3): p. 203-15

Kobari, L., et al., In vitro and in vivo evidence for the long-term multilineage (myeloid, B, NK, and T) reconstitution capacity of ex vivo expanded human CD34(+) cord blood cells. Exp Hematol, 2000. 28(12): p. 1470-80

Lemischka, I. R., Microenvironmental regulation of hematopoietic stem cells. Stem Cells, 1997. 15 Suppl 1: p. 63-8

Lichtman, M. A., The ultrastructure of the hemopoietic environment of the marrow: a review. Exp Hematol, 1981. 9(4): p. 391-410

Lyons, A. B. and C. R. Parish, Determination of lymphocyte division by flow cytometry. J Immunol Methods, 1994. 171(1): p. 131-7.

Malik, P., et al., An in vitro model of human red blood cell production from hematopoietic progenitor cells. Blood, 1998. 91(8): p. 2664-71

Marden, M. C., et al., T-state hemoglobin with four ligands bound. Biochemistry, 1988. 27(5): p. 1659-64

Morrison et al., 11 Annu. Rev. Cell Dev. Biol., 35-71 (1995)

Neildez-Nguyen, T. M., et al., Human erythroid cells produced ex vivo at large scale differentiate into red blood cells in vivo. Nat Biotechnol, 2002. 20(5): p. 467-72

Ogawa, M., Differentiation and proliferation of hematopoietic stem cells. Blood, 1993. 81(11): p. 2844-53

Ohneda, O. and V. L. Bautch, Murine endothelial cells support fetal liver erythropoiesis and myelopoiesis via distinct interactions. Br J Haematol, 1997. 98(4): p. 798-808

Panzenbock, B., et al., Growth and differentiation of human stem cell factor/erythropoietin-dependent erythroid progenitor cells in vitro. Blood, 1998. 92(10): p. 3658-68

Papassotiriou, I., et al., Gamma chain heterogeneity: determination of Hb F composition by perfusion chromatography. Hemoglobin, 1998. 22(5-6): p. 469-81

Pic, P., R. Ducrocq, and R. Girot, [Separation of hemoglobins F, Fac, S, C, A1c and determination of hemoglobin F using high performance liquid chromatography]. Ann Biol Clin (Paris), 1994. 52(2): p. 129-32

Pittenger, Science, 1999 284, p 143-147

Prockop, D. J. Marrow stromal cells as stem cells for nonhematopoietic tissues. Science 276, 71-4 (1997).

Qiu, L. B., et al., Extruded erythroblast nuclei are bound and phagocytosed by a novel macrophage receptor. Blood, 1995. 85(6): p. 1630-9

Reyes, Blood 2001, 98, 2615-2625

Sato, T., et al., Erythroid progenitors differentiate and mature in response to endogenous erythropoietin. J Clin Invest, 2000. 106(2): p. 263-70

Simmons P J, Blood 1991, 78, p 55-62

Sui, X., et al., Erythropoietin-independent erythrocyte production: signals through gp130 and c-kit dramatically promote erythropoiesis from human CD34+ cells. J Exp Med, 1996. 183(3): p. 837-45

Suzuki J, et al. Leukemia 1992, 6 (5): p. 452.

Sekiya I . . . Prockop, PNAS 2002, vol 99, p 4397

Verfaillie, C. M., Soluble factor(s) produced by human bone marrow stroma increase cytokine-induced proliferation and maturation of primitive hematopoietic progenitors while preventing their terminal differentiation. Blood, 1993. 82(7): p. 2045-53 von Lindern, M., et al., The glucocorticoid receptor cooperates with the erythropoietin receptor and c-Kit to enhance and sustain proliferation of erythroid progenitors in vitro. Blood, 1999. 94(2): p. 550-9

Wada, H., et al., Expression of major blood group antigens on human erythroid cells in a two phase liquid culture system. Blood, 1990. 75(2): p. 505-11

Yanai, N., Y. Sato, and M. Obinata, A new type-II membrane protein in erythropoietic organs enhances erythropoiesis. Leukemia, 1997. 11 Suppl 3: p. 484-5.

Zermati, Y., et al., Transforming growth factor inhibits erythropoiesis by blocking proliferation and accelerating differentiation of erythroid progenitors. Exp Hematol, 2000. 28(8): p. 885-94

The invention claimed is:

1. An in vitro method for producing enucleated erythrocytes, said method comprising the steps of:
    a) culturing for 6 to 11 days CD34+ haematopoietic stem cells in a culture medium that comprises stem cell factor (SCF), interleukin-3 (IL3), and erythropoietin (EPO);
    b) culturing for 3 to 5 days the cells obtained in step a), in a culture medium that comprises at least EPO and is in contact with supporting cells, wherein the supporting cells are MS-5 stromal cells or mesenchymal stromal cells; and
    c) culturing for 2 to 14 days the cells obtained in step b), while maintaining contact with said supporting cells, in the absence of any haematopoietic growth factor until red blood cells selected from the group consisting of reticulocytes, mature red blood cells, and combinations thereof are obtained.

2. The method of claim 1, wherein the supporting cells are genetically modified cells.

3. The method of claim 1, wherein the haematopoietic stem cells cultured in step a) are genetically modified cells.

4. The method of claim 3, wherein the cells are capable of expressing an exogenous nucleotide sequence of interest.

5. The method of claim 4, wherein the sequence of interest encodes a haemoglobin type.

6. The method of claim 1, wherein step c) is performed until reticulocytes are obtained.

7. The method of claim 1, wherein step c) is performed until mature red blood cells are obtained.

8. The method of claim 1, wherein
    a) the culturing of CD34+ haematopoietic stem cells is performed in a culture medium that comprises SCF, IL-3, and EPO for 8 days;
    b) the culturing of the cells obtained in step a) is performed in a culture medium that comprises EPO, and is in contact with MS-5 stromal cells or mesenchymal stromal cells, for 3 days; and
    c) the culturing of the cells obtained in step b), are maintained in contact with the MS-5 stromal cells or mesenchymal stromal cells, in the absence of any haematopoietic growth factor, for 4 days, whereby reticulocytes are obtained, or for 7 days, whereby mature red blood cells are obtained.

9. The method of claim 1, wherein step c) is performed until a mixture of reticulocytes and mature red blood cells are obtained.

10. The method of claim 1, wherein the CD34+ haematopoietic stem cells cultured in step a) are CD34+ cord blood cells.

11. The method of claim 1, wherein the CD34+ haematopoietic stem cells cultured in step a) are obtained by leukapheresis.

* * * * *